United States Patent [19]
Glock et al.

[11] Patent Number: 5,593,936
[45] Date of Patent: Jan. 14, 1997

[54] HYDRATED NIOBIUM OXIDE AND HYDRATED TANTALUM OXIDE CATALYSTS, THEIR PREPARATION AND A PROCESS FOR PREPARING N-ALKYLATED ANILINES USING THESE CATALYSTS

[75] Inventors: Volker Glock, Krefeld; Ursula Pentling, Kempen; Bernd Pennemann, Köln; Joerg-Dietrich Jentsch, Mülheim; Eberhard Zirngiebl, Köln; Horst Köller, Krefeld, all of Germany

[73] Assignee: Bayer Aktiengesellschaft, Leverkusen, Germany

[21] Appl. No.: 410,466

[22] Filed: Mar. 24, 1995

[30] Foreign Application Priority Data

Mar. 31, 1994 [DE] Germany ............... 44 11 234.3

[51] Int. Cl.$^6$ ..................................... B01J 23/20
[52] U.S. Cl. ..................... 502/354; 502/353; 502/182
[58] Field of Search ............................ 502/182, 353, 502/354

[56] References Cited

U.S. PATENT DOCUMENTS 4,973,569  11/1990  Bowman et al. .............. 502/209
5,166,440  11/1992  Immel et al. ................. 564/401

FOREIGN PATENT DOCUMENTS 135145  3/1985  European Pat. Off. .
433811  6/1991  European Pat. Off. .
509493  10/1992  European Pat. Off. .

*Primary Examiner*—Shrive Beck
*Assistant Examiner*—Timothy H. Meeks
*Attorney, Agent, or Firm*—Sprung Horn Kramer & Woods

[57] ABSTRACT

New hydrated niobium oxide and hydrated tantalum oxide catalysts containing pores having diameters in the range from 0.4 to 10,000 nm are characterized in that the volume of the pores of the catalyst having a diameter of from 100 to 1000 nm is at least 30% of the total pore volume of the catalyst. The catalysts can be prepared by mixing hydrated niobium oxide or hydrated tantalum oxide with an inert solid and converting this mixture into a solid pellet form, with the pressure in the apparatus for preparing catalysts in pellet form being set in such a way that the volume of the pores of the catalyst having a diameter of from 100 to 1000 nm is at least 30% of the total pore volume of the catalyst. Such catalysts are particularly suitable for preparing N-alkylanilines from anilines and alkanols.

4 Claims, No Drawings

HYDRATED NIOBIUM OXIDE AND HYDRATED TANTALUM OXIDE CATALYSTS, THEIR PREPARATION AND A PROCESS FOR PREPARING N-ALKYLATED ANILINES USING THESE CATALYSTS

The invention relates to hydrated niobium oxide and hydrated tantalum oxide catalysts having particular pores and lateral fracture harnesses, their preparation and a process for preparing N-alkylated anilines using these catalysts.

N-alkylated aromatic amines are starting materials for producing dyes, pesticides, urethanes, drugs and crop protection agents. Furthermore, they are used as mineral oil additives and as additives for surface coatings and other polymer systems.

Various methods are known for preparing secondary and tertiary aromatic amines. Thus, it is already known that N-alkylated aromatic amines can be prepared by reacting aromatic amines with alkanols or dialkyl ethers in the gas phase over heterogeneous catalysts.

The prior art for preparing N-alkylated anilines over heterogeneous catalysts is described, for example, in EP-A 433 811. This document also describes the use of hydrated niobium oxide and hydrated tantalum oxide as catalyst.

To prepare granulated materials, extrudates or spheres, the catalyst can be applied to a support or provided with a binder and granulated or extruded. It can also be provided with a lubricant and converted into a pellet form by tabletting.

For use of the catalyst in a fixed-bed gas-phase reactor, it is important that the granulated catalyst has sufficient strength. It is known that catalysts having insufficient strength can disintegrate because of their own weight, pressure loss in the reactor, thermal stressing and other causes, which can then lead to very non-uniform pressure losses in fixed beds and finally to blocking of the reactor. Catalysts having low strength therefore have only a short lifetime and are not suitable for industrial use. A measure of the strength is the so-called lateral fracture hardness. The determination of the lateral fracture hardness can be carried out using conventional measuring instruments, e.g. using those supplied commercially by Schleuniger.

Catalysts having fracture hardnesses below 20N are unsuitable for industrial use, since experience has shown that they do not withstand the stresses occurring during charging and operation of an industrial reactor (see Comparative Example 2). It is known that the activity of a mechanically shaped catalyst and its strength are inversely proportional and that usually an increase in the strength causes a decrease in the catalytic activity.

Hydrated niobium oxide and hydrated tantalum oxide catalysts have now been found, which catalysts contain pores having diameters in the range from 0.4 to 10,000 nm and are characterized in that the volume of the pores of the catalyst having a diameter of from 100 to 1000 nm makes up at least 30% of the total pore volume of the catalyst. Preferably, the proportion of these pores is at least 33% of the total pore volume and particularly preferably at least 36%.

Catalysts of the invention generally have lateral fracture hardnesses of over 20N, preferably over 25N.

The pore volume and the pore diameter distribution can be determined in a known manner, for example using a mercury porosimeter.

Catalysts of the invention can be prepared by mixing hydrated niobiumoxide or hydrated tantalum oxide with an inert solid, for example graphite, and converting such mixtures into solid pellet form, e.g. by tabletting using a tabletting press. To obtain catalysts in accordance with the invention, it is generally necessary to set the pressure in the apparatus for preparing catalysts in pellet form in such a way that the volume of the pores of the catalyst having a diameter of from 100 to 1000 nm is at least 30% of the total pore volume. To set a suitable pressure in the apparatus for preparing catalysts in pellet form, routine trials can be carried out beforehand, in which pressures can be varied, for example, in the range from 500 to 50,000 kg/cm$^2$ and account should be taken of the fact that the application of higher pressures lowers the proportion of pores having diameters in the range from 100 to 1000 nm.

The hydrated niobium oxide and hydrated tantalum oxide catalysts thus obtained have the lateral fracture hardness required for industrial use and at the same time have a significantly higher activity than catalyst shown hitherto. The catalysts of the invention can be used, for example, for dehydrogenations, oxidative dehydrogenations, ammonoxidations, polymerizations, isomerizations, decompositions (for example of $NO_x$), Fischer-Tropsch syntheses, hydrogenations and alkylations, in particular N-alkylations.

It has furthermore been found that catalysts of the invention are particularly suitable for the preparation of N-alkylanilines from anilines and alkanols. For example, this process can be carried out using anilines of the formula (I)

where

R$^1$ and R$^2$ are, independently of one another, hydrogen, $C_1$–$C_4$-alkyl, $C_1$–$C_4$-alkoxy, fluorine, chlorine, bromine or cyano and R$^3$ is hydrogen, $C_1$–$C_{12}$-alkyl or $C_3$–$C_7$-cycloalkyl and alkanols of the formula

where

R$^4$ is $C_1$–$C_{12}$-alkyl or $C_3$–$C_7$-cycloalkyl to obtain N-alkylanilines of the formula (III)

where

R$^1$ to R$^4$ are as specified above.

This reaction can be carried out in the liquid phase or in the gas phase, for example at temperatures of from 160° to 400° C. and at molar ratios of alkanol to anilines of from 0.5 to 10:1. The above-described process for preparing N-alkylanilines has the surprising advantage that it permits the achievement of high space-time yields and the amounts of unreacted starting materials can be kept small. The catalyst used has sufficient strength for a process to be carried out in industry.

The percentages given are, unless otherwise indicated, by weight.

EXAMPLES

COMPARATIVE EXAMPLE 1

A stainless steel reaction tube having an internal diameter of 25 mm was charged with 118.5 g of tabletted hydrated niobiumoxide (diameter 6.4 nm) in which 24% of the total pore volume was made up by the pores having a diameter of from 100 to 1000 nm and which had a mean lateral fracture hardness of 148N. A gas mixture of ethanol and unsubstituted aniline in a molar ratio of 1:4 was passed at 261° C. through this catalyst bed at a rate of 1.35 g/ml h. The reaction product formed over the course of 48 hours had the following composition according to gas chromatography:

Aniline: 17.47% by area

N-ethylaniline: 32.51% by area

N,N-diethylaniline: 47.90% by area

Byproducts: 2.12% by area

COMPARATIVE EXAMPLE 2

Hydrated niobiumoxide was, with the addition of 3.5% of graphite, pressed in a laboratory press to form tablets which have a diameter of 5 mm, a mean lateral fracture hardness of 14N and in which 56% of the total pore volume is made up by pores having a diameter of from 100 to 1000 nm. 89 g of this catalyst were tested under the conditions of Comparative Example 1, but at a temperature of 265° C., and after 168 hours a reaction mixture having the following composition was obtained:

Aniline: 8.22% by area

N-ethylaniline: 39.09% by area

N,N-diethylaniline: 51.12% by area

Byproducts: 1.57% by area

The strength of this catalyst was not sufficient for industrial use since even at a height of the fixed bed of 3 m it broke under its own weight.

EXAMPLE 1

Hydrated niobium oxide was, with the addition of 4% of graphite, pressed to form tablets on an industrial press in such a way that the tablets have a diameter of 5 mm, a mean lateral fracture hardness of 41N and 42% of the total pore volume is made up of pores having a diameter of from 100 to 1000 nm. 106.3 g of the catalyst were tested under the conditions of Comparative Example 1. This gave a reaction mixture having the following composition:

Aniline: 7.23% by area

N-ethylaniline: 35.05% by area

N,N-diethylaniline: 55.66% by area

Byproducts: 2.06% by area

In contrast to Comparative Example 2, this catalyst had sufficient strength for industrial use, since it did not break under its own weight at a fixed bed height of 3 m.

EXAMPLE 2

597 kg of the catalyst from Example 1 were charged into a tube-bundle reactor comprising 350 tubes having a diameter of 2.5 cm each and a length of 3.5 m. A mixture of ethanol and aniline in a molar ratio of 1:3 was passed at 262° C. over the catalyst bed at a rate of 600 kg/h. The reaction product formed over the course of 24 hours had the following composition according to gas chromatography:

Aniline: 4.23% by area

N-ethylaniline: 38.81% by area

N,N-diethylaniline: 53.99% by area

Byproducts: 2.97% by area

After 500 hours, the catalyst still displayed no significant mechanical defects.

What is claimed is:

1. A catalyst comprising at least one oxide selected from the group consisting of hydrated niobium oxide and hydrated tantalum oxide, having pores with diameters in the range from 0.4 to 10,000 nm, in which catalyst the volume of pores having a diameter of from 100 to 1,000 nm makes up at least 30% of the total pore volume of the catalyst, the catalyst having a lateral fracture hardness of over 20N.

2. A catalyst according to claim 1, wherein the volume of the pores having a diameter of from 100 to 1,000 nm make up at least 33% of the total pore volume.

3. A process for preparing a catalyst comprising at least one oxide selected from the group consisting of hydrated niobium oxide and hydrated tantalum oxide, having pores with diameters in the range from 0.4 to 10,000 nm, which process comprises mixing at least one oxide selected from the group consisting of hydrated niobium oxide and hydrated tantalum oxide with an inert solid, and pressing the mixture to convert it into pellets in such a way that the volume of the pores having a diameter of from 100 to 1,000 nm makes up at least 30% of the total pore volume of the finished catalyst.

4. A catalyst according to claim 1, in the form of tablets of approximately 5 mm in diameter.

\* \* \* \* \*